(12) United States Patent
Hug et al.

(10) Patent No.: US 8,420,677 B2
(45) Date of Patent: Apr. 16, 2013

(54) USE OF 3,3'-DIINDOLYLMETHANE

(75) Inventors: Hubert Hug, Efringen-Kirchen (DE); Bernd Mussler, Lahr (DE); Daniel Raederstorff, Flaxlanden (FR); Ying Wang-Schmidt, Stallkon (CH)

(73) Assignee: DSM IP Assets B.V., Heerlen (NL)

( * ) Notice: Subject to any disclaimer, the term of this patent is extended or adjusted under 35 U.S.C. 154(b) by 142 days.

(21) Appl. No.: 12/918,143

(22) PCT Filed: Feb. 19, 2009

(86) PCT No.: PCT/EP2009/051959
§ 371 (c)(1), (2), (4) Date: Nov. 8, 2010

(87) PCT Pub. No.: WO2009/103755
PCT Pub. Date: Aug. 27, 2009

(65) Prior Publication Data
US 2011/0190367 A1    Aug. 4, 2011

(30) Foreign Application Priority Data

Feb. 19, 2008   (EP) .................................. 08003002

(51) Int. Cl.
*A61K 31/41*    (2006.01)
*A61K 31/405*   (2006.01)

(52) U.S. Cl.
USPC ........................... 514/359; 514/415; 514/427

(58) Field of Classification Search .................. 514/359, 514/415, 427
See application file for complete search history.

(56) References Cited

U.S. PATENT DOCUMENTS
2004/0147585 A1    7/2004   Jacobs et al.

FOREIGN PATENT DOCUMENTS
WO    WO 03/035621    5/2003
WO    WO 2006/083458   8/2006

OTHER PUBLICATIONS
International Search Report for PCT/EP2009/051959, mailed May 14, 2009.

*Primary Examiner* — Renee Claytor
(74) *Attorney, Agent, or Firm* — Nixon & Vanderhye P.C.

(57) ABSTRACT

Use of DIM and/or its derivatives for prevention, treatment and/or delay of age-related hearing loss in mammals.

11 Claims, 1 Drawing Sheet

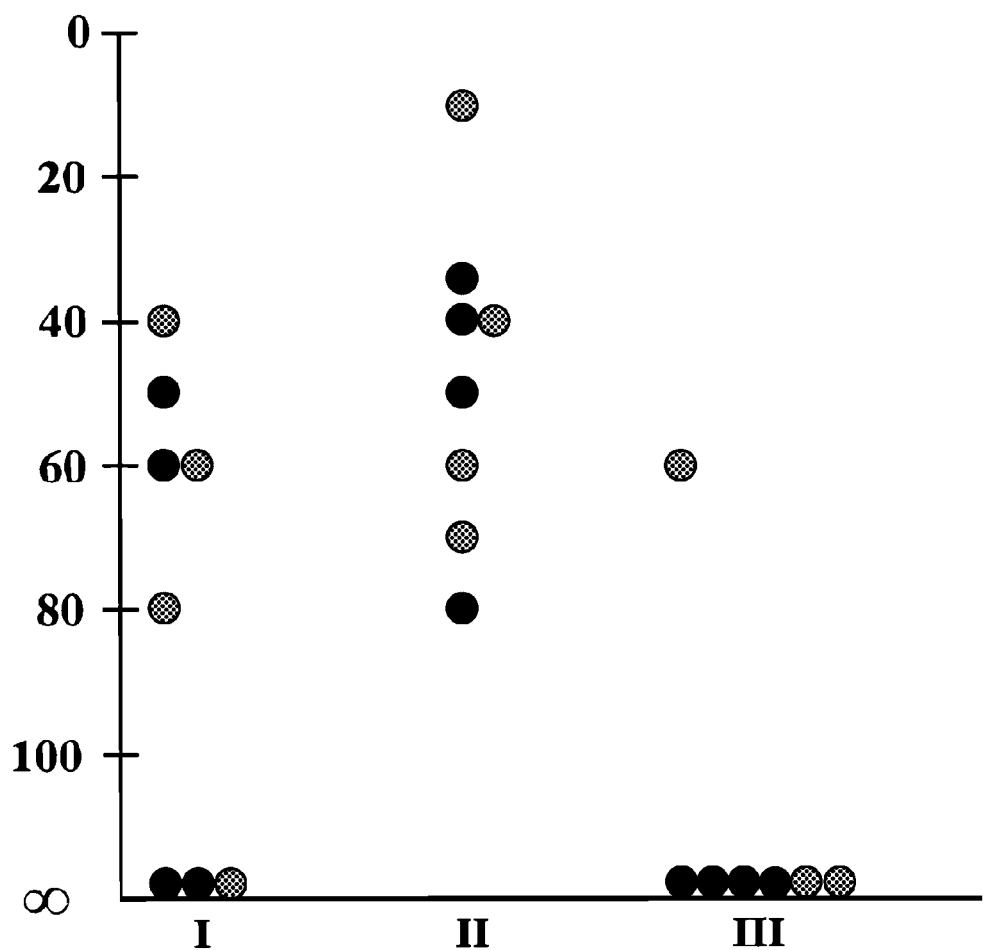

USE OF 3,3'-DIINDOLYLMETHANE

This application is the U.S. national phase of International Application No. PCT/EP2009/051959 filed 19 Feb. 2009, which designated the U.S. and claims priority to EP Application No. 08003002.6 filed 19 Feb. 2008, the entire contents of each of which are hereby incorporated by reference.

The present invention relates to a novel use of 3,3'-diindolylmethane (CAS1968-05-4) and/or its derivatives; in particular it relates to the use of 3,3'-diindolylmethane and/or its derivatives in the form of a pharmaceutical and/or nutritional composition to prevent and treat age-related hearing loss, also called presbycusis.

3,3'-diindolylmethane (DIM) is a known plant indol derivative which can be found in cruciferous vegetables including cabbage, broccoli, Brussels sprouts, and cauliflower. DIM is formed from a condensation reaction of two molecules of its precursor, indole-3-carbinol (I3C).

DIM has been shown to have several beneficial properties such as cardio and brain protective activities, cancer prevention, and benefits for perimenopausal women in premenstrual syndrome (PMS), endometriosis, and cervical dysplasia. Women on estrogen replacement (HRT) also benefit from DIM supplementation, as well as men with estrogen-related conditions, including prostate hypertrophy. I3C and DIM have also been shown to have multiple anti-cancer effects both in in-vivo and in-vitro models.

Approximately one third of the American population in the age of 65 to 75 suffers from hearing loss and 50% of people above 75 have some degree of hearing loss, as indicated by the National Institute of Deafness and Other Communication Disorders (NIDCD).

The ear is made up of three parts: the outer ear (pinna or auricle), the middle ear, which includes the eardrum (tympanic membrane), and the inner ear (cochlea). Sound enters the outer ear and strikes the eardrum, causing it to vibrate. The eardrum's vibrations are amplified through the chamber of the middle ear along three tiny interconnected bones, hammer (malleus), anvil (incus), and stirrup (stapes), which pass on the vibrations of sound waves to the cochlea.

Age-related hearing loss, or presbycusis, affecting many species, is characterized by an age-related progressive decline of auditory function, and is an irreversible process.

A hearing loss (also hearing impairment) exists when an individual is not sensitive to the sounds normally heard by its kind.

It is not yet fully understood why hearing loss occurs, and many factors have been demonstrated to be the risk factor. Hearing loss arises mainly from the degeneration of hair cells or spiral ganglion (SG) cells in the cochlea. When the tiny hairs inside the cochlea are damaged or die, which often happens as people age, hearing loss occurs. Structural changes in the inner ear, such as the degeneration of sensory cells, auditory neurons and cells of the stria vascularis, also contribute to hearing loss. In humans, the cochlear degeneration can be attributed to the accumulated effects of numerous insults including exposure to acoustic trauma and ototoxic drugs. However, hearing loss is a common phenomenon in mammals, regardless of noise and toxin exposure. In addition, hereditary factors, blood supply dysfunction due to heart disease, high blood pressure, diabetes, or other circulatory problems are all risk factors leading to hearing loss.

Reactive oxygen species (ROS) are one of the causes of age-related cellular degeneration throughout the organism. Free radicals or ROS, a product of cellular respiration, normally exist in three forms: the superoxide anion ($O_2^-$), hydrogen peroxide ($H_2O_2$) and the hydroxyl radical (OH). These species are very unstable, reacting with and thereby damaging proteins, lipids and DNA. Endogenous, cellular enzymes, such as catalase, copper/zinc and manganese superoxide dismutase (SOD1 and SOD2, respectively) and peroxidase convert ROS to neutral, non-reactive molecules. Accordingly these substances are important contributors to cellular stability and survival. The importance of these endogenous antioxidants in cochlear cell survival was demonstrated in SOD1 transgenic mice in which early hearing loss and degeneration of auditory neurons and hairs cells was observed (McFadden et al., 1999a, McFadden et al., 1999b, McFadden et al., 2001 and Keithley et al., 2005). The stria vascularis is much less affected, so it seems that each oxidative tissue may use different antioxidant mechanisms to clear ROS. Although the absence of SOD1 results in a great deal of degeneration, half as much SOD1 was sufficient to maintain hearing and cochlear morphology (Keithley et al., 2005). Mitochondrial DNA (mtDNA), located near the site of oxidative phosphorylation in the inner membrane of mitochondria, is especially vulnerable (Miguel et al., 1980, Barja, 2004 and Sastre et al., 2003).

Accordingly the use of antioxidants as supplement for preventing age-related hearing loss was proposed.

Nevertheless many hearing impaired individuals use certain assistive devices in their daily lives, such as hearing aids, which amplify the incoming sound. Hearing aids may alleviate some of the problems caused by hearing impairment, but are often insufficient. In addition to hearing aids there exist cochlear implants of increasing complexity and effectiveness. These are useful in treating mild to profound hearing impairment.

Currently, no dietary or medical interventions exist which have proven efficacy on treatment or prevention of hearing loss.

Magnesium was used to protect ears from noise-induced hearing loss. It is not clear how magnesium might protect hearing and studies in animals suggest that magnesium deficiency can increase the stress on cells involved with hearing and thereby make them more susceptible to damage caused by intense noise. However, human magnesium deficiency is rare, so it is possible that supplemental magnesium acts in some entirely different way.

Ginkgo extract was used to treat sudden hearing loss, or so called unilateral idiopathic sudden hearing loss. Ginkgo extract, which is shown to improve circulation, has been tested as treatment for the sudden hearing loss. In a double-blind study, ginkgo was compared to pentoxifylline, a circulation-enhancing drug used in Germany for the treatment of sudden hearing loss and the results indicate that ginkgo was at least as effective as the medication.

Antioxidant supplementation was suggested as promising measures for hearing loss prevention, and commonly used antioxidants are citrus bioflavonoids, coenzyme Q10, lipoic acid, lutein, lycopene, oligomeric proanthocyanidins (OPCS), vitamin C and vitamin E. However, there is lack of scientific evidence on the effect of antioxidants in preventing hearing loss.

It was therefore an object of the following invention to provide a composition for the prevention or delay of age-related hearing loss.

It has surprisingly been found that the object of the present invention is achieved by a composition for the prevention, treatment and/or delay of age-related hearing loss in mammals characterized in that the composition contains 3,3'-diindolylmethane.

The terms "3,3'-diindolylmethane" and "DIM" as used herein also include derivatives of 3,3'-diindolylmethane according to the following chemical structure:

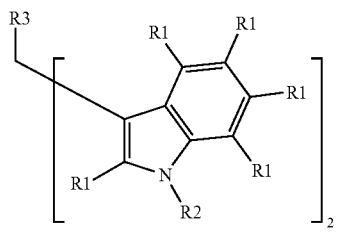

wherein the residues R1, R2 and R3 are independently chosen from the following groups:

R1: H, $OCH_3$, $CH_3$ with the provisio that at least 3 of the 5 residues R1 are H;
R2: $CH_3$—$(CH_2)_n$—$CH_3$ wherein n=0-16;
R3: H, $CH_3$—$(CH_2)_n$—R4 wherein n=0-16 and R4=H or COOH;

According to the present invention 3,3'-diindolylmethane may be of synthetic origin or it may be isolated from plant extracts, such as extracts of cruciferous vegetables (including their seeds and/or sprouts). It may also be advantageous to use extracts containing 3,3'-diindolylmethane, for example extracts obtainable from cruciferous vegetables. Based on the particular extraction procedure the amount of phenolic compounds in a plant extract can be easily adjusted by a person skilled in the art. It is preferred if the amount of 3,3'-diindolylmethane in a plant extract according to the present invention is in the range of from 20 to 80% by weight, more preferred from 30 to 50% by weight, each based on the total weight of the extract.

The composition according to the invention is preferably a dietary supplement, a food or feed additive, a functional food or feed, a food or feed premix, and/or a beverage.

While for the purpose of the present invention mammals are preferably humans, the invention is not limited to humans but includes other mammals, such as dromedaries, camels, elephants, and horses and pets such as dogs, cats and/or small animals.

For the purposes of the invention, 3,3'-diindolylmethane (DIM) may be administered to, e.g., a human adult (weighing about 70 kg) in an amount of up to about 10 to 1000 mg/day in one or several dosage units or servings. In a particular embodiment of the invention, the dosage for a human adult (weighing about 70 kg) is up to about 500 mg/day, especially from 30 to 300 mg/day. If administered in a food or beverage the amount of DIM contained therein is suitably no less than about 100 mg per serving. If DIM is administered as a pharmaceutical formulation such formulation may contain up to about 500 mg per solid dosage unit, e.g. per capsule.

The term "serving" as used herein denotes an amount of food and/or beverage normally ingested by a human adult with a meal at a time and may range, e.g., from about 100 g to about 500 g food and/or beverage.

The composition according to the present invention can preferably be a nutraceutical composition. The term "nutraceutical" as used herein denotes usefulness in both, the nutritional and pharmaceutical field of application. Thus, "nutraceutical compositions" according to the present invention can serve as supplements to food, feed and beverages, dietary supplements and as pharmaceutical formulations which may be solid—such as capsules—or liquid—such as solutions or suspensions. It is evident from the foregoing that the term "nutraceutical composition" also comprises food, feed and beverages containing DIM.

A multi-vitamin and mineral supplement may be added to the compositions according to the present invention, e.g. to maintain a good balanced nutrition or to obtain an adequate amount of an essential nutrient missing in some diets. The multi-vitamin and mineral supplement may also be useful for disease prevention and protection against nutritional losses and deficiencies due to lifestyle patterns and common inadequate dietary patterns.

The composition according to the present invention can preferably be a food or beverage composition. Beverages can be e.g. sports drinks, energy drinks or other soft drinks, or any other suitable beverage preparation, e.g. yoghurt drinks, hot beverages or soups.

In a preferred embodiment of the present invention the beverage is an "instant beverage", i.e. a beverage which is produced—normally by the consumer themselves—by stirring a powder into a liquid, usually milk or water.

By "sports drink" a beverage is meant which is consumed before, during and/or after physical exercise, mainly to hydrate as well as to (re-) store electrolytes, sugar and other nutrients. Sports drinks are usually isotonic, meaning they contain the same proportions of nutrients as found in the human body.

Energy drinks are beverages which contain (legal) stimulants, vitamins (especially B vitamins) and/or minerals with the intent to give the user a burst of energy. Common ingredients include caffeine, guarana (caffeine from the Guarana plant) and/or taurine, various forms of ginseng, maltodextrin, inositol, carnitine, creatine, glucuronolactone, coenzyme Q10 and/or ginkgo biloba. Some may contain high levels of sugar, or glucose, whereas others are sweetened completely or partially with a sugar alcohol and/or an artificial sweetener like Ca-cyclamate or Aspartame. Many such beverages are flavored and/or colored.

A soft drink is a drink that does not contain alcohol. In general, the term is used only for cold beverages. Hot chocolate, tea, and coffee are not considered soft drinks. The term includes carbonated and non-carbonated drinks, e.g. mineral water or so-called "near water drinks", i.e. water-based beverages which have an additional benefit, e.g. a special flavor and/or further (functional) ingredients. One simple example for a "near water drink" is a mixture of water with very little juice.

If the composition is prepared in form of one of the following food articles it is according to the present invention advantageous if the amount of DIM in the composition is selected from the ranges given in the following table:

| Food Category | typical serving size | Preferred amount DIM in beverage or food (most preferred range in brackets) |
|---|---|---|
| Beverages (final product) (e.g. soft drinks, juices (fruit and/or vegetable), teas, soups) | 200 mL, preferred 3 servings a day | 50-1000 mg/L (150-750) 10-200 mg/serving, (30-150) 30-600 mg/day (90-450) |
| Dairy Products (e.g. milk shakes, joghurts, joghurt drinks, ice creams) | 150 g | 50-1000 mg/kg (165-660) 8-150 mg/serving (25-100) |
| Sweets and confectionaries (e.g. chocolates, candies, mints, jellies, cookies) | 1 to 3 pieces of 5 g each | 2000-40'000 mg/kg (6000-30'000) 10-200 mg/piece (30-150) |
| other food items (e.g. breakfast cereals, | per day 25 g | 10-600 mg/day (30-450) 400-8000 mg/kg (1200-6000) |

-continued

| Food Category | typical serving size | Preferred amount DIM in beverage or food (most preferred range in brackets) |
|---|---|---|
| muesli bars, snacks, pasta sauces) | | 10-200 mg/serving (30-150) |

If the composition is prepared in form of a capsule it is according to the present invention advantageous if the amount of DIM is selected from the ranges given in the following table:

| Category | typical dosage | Preferred amount DIM per capsule (most preferred in brackets) |
|---|---|---|
| Capsules | 1-2 × per day | 20-600 mg/capsule (50-450) |

The invention is further illustrated by FIG. 1:

FIG. 1 shows the effect of tested compounds on age related hearing loss (presbycusis) in D257A mice, an accelerated ageing mouse model, which exhibit significantly reduced hearing function.

The auditory-evoked brain stem response threshold (hearing threshold) in decibels (dB) 8 kHz is shown on the y-axis. Black circles represent male, grey circles female D257A mice. ∞ means that no response was obtained.

Values are shown for:
I: Placebo control;
II: DIM;
III: EGCG;

The invention is further illustrated by the following examples.

EXAMPLES

The efficacy of DIM was demonstrated as shown by tests set forth below. The test system was D257A−/− (D257A) mice that express a proofreading-deficient version of the mitochondrial DNA polymerase γ (POLG). These mice display features of accelerated aging including age related hearing loss (presbycusis). Hearing loss can be monitored by an elevation in auditory-evoked brainstem response (Kujoth et al., Science 309, 481-484, 2005).

Example I

Compound Feeding

Heterozygous D257A (−1+) mice were bred to generate homozogous D257A (−/−) mice, denoted D257A hereafter. Animals were identified with specific numbering and ear clippings. D257A mice were placed in various dietary regimens following PCR based genotyping and weaning at 3 weeks of age. Mice received a diet based on AIN-93M maintenance purified diet (TestDiet, Richmond, USA), with neither no supplementation (Control group), or supplementation with DIM (40 mg/kg, BioResponse LLC Boulder, Colo.), (−)-epigallocatechin gallate, or (EGCG) (300 mg/kg, DSM Nutritional Products, Switzerland).

Assessment of Hearing Function

Hearing function was tested in 9 month-old D257A mice receiving the various compounds. Auditory brainstem responses (ABRs) were measured with a tone burst stimulus (8, 16 and 32 kHz) using an ABR recording system (Intelligent Hearing System, Miami Fla.). Animals were anesthetized with a mixture of xylazine hydrochloride (10 mg/kg, i.m.) and ketamine hydrochloride (40 mg/kg, i.m.), and needle electrodes were placed subcutaneously at the vertex (active electrode), beneath the pinna of the measured ear (reference electrode), and beneath the opposite ear (ground). The stimulus duration, presentation rate, and rise/fall time was 3 ms, 19.3/s, and 1 ms respectively. Responses of 1024 sweeps were averaged at each intensity level (5 dB steps) to access the hearing threshold. The hearing threshold was defined as the lowest intensity level at which a clear reproducible waveform was visible in the trace. Means of ABR thresholds were compared at 8, 16 and 32 kHz.

Results

Age-related loss of auditory function and cochlear degeneration in D257A mice at the age of 9 months were described (Kujoth et al., Science. 2005 Jul. 15; 309(5733):481-4). Based on these data we tested whether DIM, or (−)-epigallocatechin gallate (EGCG), could help to prevent presbycusis.

At the frequency of 8 kHz no deaf mice were present of the 8 mice treated with DIM. In the control group 3 out of 8 mice were deaf. In the DIM treated group the hearing threshold was approximately 10 dB. In the control group it was approximately 40 dB. The amount of deaf mice was even higher in the mice treated with EGCG (see FIG. 1). At 32 kH the percentage of deaf mice was also significantly lower in the DIM group compared to the control group and the other tested compounds.

DIM supplementation from early age on, showed a protective effect on age related hearing loss. Since no other antioxidant showed a similar effect, we postulate that DIM is unique in the perspective that it provides additional protection than antioxidation, and could be used in nutraceutical or pharmaceutical composition for treating or preventing age-related hearing loss.

Pharmaceutical compositions may be prepared by conventional formulation procedures.

Example 1

Soft Gelatin Capsule

Soft gelatin capsules are prepared by conventional procedures containing as active ingredient 100 to 200 mg of DIM per capsule.

Example 2

Hard Gelatin Capsule

Hard gelatin capsules are prepared by conventional procedures containing as active ingredient 100 to 200 mg of DIM per capsule.

Example 3

Food items may be prepared by conventional procedures containing DIM in an amount of 30 mg to 300 mg per serving. Examples of such food items are soft drinks, bread, cookies, yoghurt, ice cream, and sweets.

The invention claimed is:
1. A method for treatment and/or delay in onset of age-related hearing loss in mammals, including administering to a mammal in need of treatment and/or delay in onset of age-related hearing loss an effective amount of 3,3'-diindolylmethane (DIM) and/or a derivative thereof.

2. The method of claim 1, which comprises administering to the mammal a composition which comprises DIM and/or a derivative thereof.

3. The method of claim 2, wherein the composition is a pharmaceutical composition.

4. The method of claim 2, wherein the composition is a nutraceutical composition.

5. The method of claim 2, wherein the composition is a food, beverage or a supplement to food or beverage.

6. The method of claim 2, wherein the composition is pet food.

7. The method of claim 1, wherein the 3,3'-diindolylmethane is of synthetic origin.

8. The method of claim 1, wherein the 3,3'-diindolylmethane is isolated from plant extracts.

9. The method of claim 1, which comprises administering the DIM and/or a derivative thereof in a dosage amount of 10 to 1000 mg per day for an adult.

10. The method of claim 9, wherein the dosage amount of DIM and/or a derivative thereof is administered in one or several dosage units or servings.

11. The method of claim 2, wherein the composition is a dairy product, a sweet product and/or a confectionary product.

* * * * *